United States Patent

Sekiuchi et al.

[11] Patent Number: 6,049,009
[45] Date of Patent: *Apr. 11, 2000

[54] PRODUCTION METHOD OF OPTICALLY ACTIVE TRANS-VINYLSULFIDE ALCOHOL

[75] Inventors: Kazuto Sekiuchi, Tatebayashi; Masahiro Imoto, Nishinomiya; Masaji Ishiguro, Takarazuka; Takashi Nakatsuka, Osaka; Rie Tanaka, Tatebayashi; Hidekazu Inoue, Ibaraki, all of Japan

[73] Assignee: Suntory Limited, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,563
[22] PCT Filed: Oct. 30, 1996
[86] PCT No.: PCT/JP96/03185
  § 371 Date: Jun. 30, 1997
  § 102(e) Date: Jun. 30, 1997
[87] PCT Pub. No.: WO97/16421
  PCT Pub. Date: May 9, 1997

[30] Foreign Application Priority Data

Oct. 31, 1995 [JP] Japan .................................. 7-283845

[51] Int. Cl.[7] .................................................. C07C 319/14
[52] U.S. Cl. ............................................................ 568/55
[58] Field of Search ........................ 568/55, 881; 546/13

[56] References Cited

U.S. PATENT DOCUMENTS 5,039,802  8/1991  Blacklock et al. .
5,264,585  11/1993  Blacklock .

FOREIGN PATENT DOCUMENTS 61-207373  9/1986  Japan .
4-224556   8/1992  Japan .
6-41012    2/1994  Japan .

OTHER PUBLICATIONS

J of Org Chem , 58(4), pp. 799–801, "Origins of the Enantioselectivity Observed in Oxazaborolidine–Catalyzed Reducions of Ketones", Feb. 1993.
CA:91:39069 abstract of Chem Lett (4) pp. 365–368 of "Reduction of beta alkylthio alpha beta unsaturated ketones with lithium tetrahydroaluminate or sodium tertahydroborate", 1979.
CA:108:75026 abstract of J Am Chem soc 109(25) pp. 7925–7926 of "A stable and easily prepared catalyst for the enantioselective reduction of ketones", 1987.
E.J. Corey et al., "A New System for Catalytic Enantioselective Reduction of A Chiral Ketones to Chiral Alcohols. Synthesis of Chiral α–Hydroxy Acids", Tetrahedron Letters, vol. 31., No. 5, pp. 611–614, (1990).

Primary Examiner—Gary Geist
Assistant Examiner—Jean F Vollano
Attorney, Agent, or Firm—Burns, Doane, Swecker & Mathis, L.L.P.

[57] ABSTRACT

A method for producing an optically active trans-vinylsulfide alcohol having the formula:

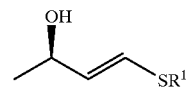

wherein $R^1$ represents an alkyl group or an aryl group, comprising the step of reducing a trans-vinylsulfide ketone with a borane reducing agent in the presence of an optically active oxazaborolidine and an additive.

17 Claims, No Drawings

PRODUCTION METHOD OF OPTICALLY ACTIVE TRANS-VINYLSULFIDE ALCOHOL

This is the national phase of PCI/JP96/03185, filed Oct. 30, 1996.

TECHNICAL FIELD

The present invention relates to a method for producing an optically active trans-vinylsulfide alcohol useful as a synthetic material of penem or carbapenem compounds.

BACKGROUND ART

Various researches have heretofore made for penem or carbapenem compounds, since they have wide and strong antimicrobial activities. In the production thereof, (1'R, 3R, 4R)-3-(1'-protected hydroxyethyl)-4-acyloxy-2-azetidinone derivatives (i.e., "acyloxyazetidinone derivatives" hereinbelow) are used as an excellent synthetic intermediate and various synthetic methods are reported (see N. Ueyama et al., JP-A-62-84057).

At present, as a production method of acyloxyazetidinone derivatives, the following method is known (see JP-A-3-127773).

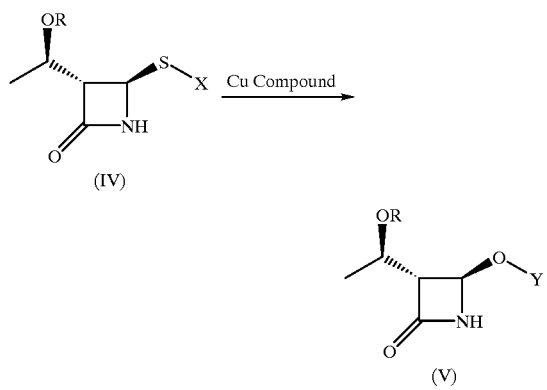

wherein OR represents a protected hydroxy group, X represents an alkyl or aryl group, and Y represents an acyl group.

Thus, this method is a method capable of safe and efficiently producing the desired acyloxyazetidinone derivatives (V) by reacting (1'R, 3S, 4R)-3-(1'-protected hydroxyethyl)-4-substituted thio-2-azetidinone derivatives (IV) (i.e., "substituted thioazetidinone derivatives" hereinbelow) with a carboxylic acid in the presence of a copper compound.

As explained above, although acyloxyazetidinone derivatives useful as a synthetic intermediate of penem or carbapenem compounds can be produced in an industrial scale from the substituted thioazetidinone derivatives as a starting material, there are various problems in the known methods for producing the starting substituted thioazetidinone derivatives.

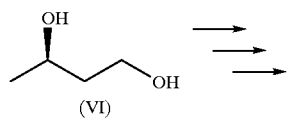

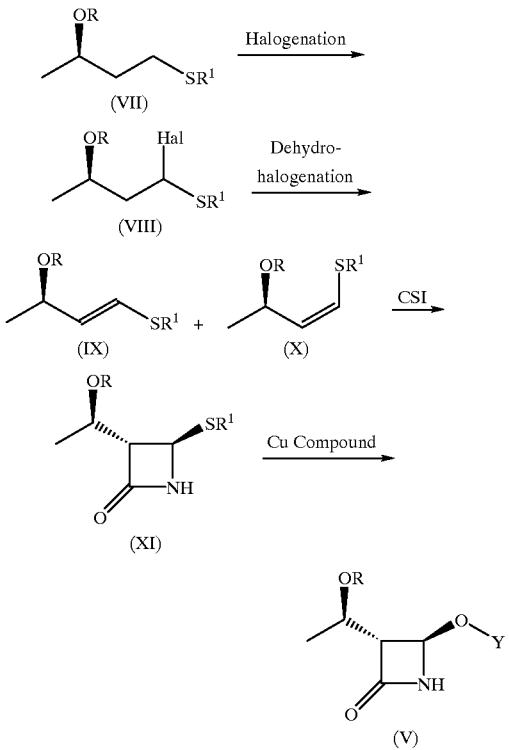

wherein Hal represents a halogen atom, $R^1$ represents an alkyl or aryl group, and OR and Y are the same as defined above.

According to the above-mentioned method (see JP-A-61-207373), an optically active 1,3-butanediol (VI) is used as a starting material and the substituted thioazetidinone derivatives (XI) can be obtained at a high yield from the cyclization reaction, with chlorosulfonyl isocyanate (CSI), of the intermediate trans-vinylsulfide (IX) obtained from the starting material through the steps of the substitution at the 1-position, the protection of the hydroxy group at the 3-position, the halogenation and the dehydrohalogenation. This is an excellent method. However, according to the above method, there are still problems that the starting optically active 1,3-butanediol is expensive and also, since the multi-step synthesis is necessary for producing the trans-vinylsulfide (IX), there are problems in the yield thereof. Furthermore, the cis-isomer (X), which is produced as a by-product during the synthesis of the trans-vinylsulfide (IX) and which is extremely difficult to separate from the trans-isomer, affects the selectivity and yield of the subsequent cyclization reaction.

Furthermore, a method for obtaining an optically active 1-substituted-3-hydroxybutane or optically active 1-substituted-3-hydroxybutene from the optical resolution of the ester derivative of racemic 1-substituted-3-hydroxybutane or racemic 1-substituted-3-hydroxybutene, respectively, with lipase (see JP-A-4-228092 and JP-A-4-228093). This method is an effective method in view of the excellent selectivity, but the maximum yield of the optically active substance is as high as 50%.

As mentioned above, there are various problems to be solved in the conventional production method for obtaining the substituted thioazetidinone derivatives and there are strong need to solve these problems.

SUMMARY OF THE INVENTION

The objects of the present invention are to solve the above-mentioned problems in the prior art and to provide a method for industrially producing an optically active trans-vinylsulfide alcohol, which is useful as a synthetic material of penem or carbapenem compounds, effectively at a low cost under mild conditions.

In accordance with the present invention, there is provided a method for producing an optically active trans-vinylsulfide alcohol having the formula (III):

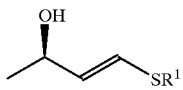

wherein $R^1$ represents an alkyl group or an aryl group, comprising the step of reducing a trans-vinylsulfide ketone having the formula (I):

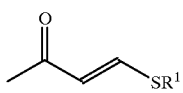

wherein $R^1$ is the same as defined above with a borane reducing agent in the presence of an optically active oxazaborolidine having the formula (II):

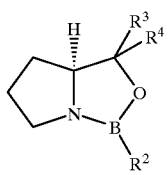

wherein $R^2$ represents a hydrogen atom, an alkyl group, an aryl group or an aralkyl group and $R^3$ and $R^4$ are the same or different and represent an alkyl group, an aryl group or an aralkyl group and an additive for controlling the reduction of the olefin double bond of the trans-vinylsulfide ketone.

BEST MODE FOR CARRYING OUT THE INVENTION

The reaction according to the present invention is carried out by adding a borane reducing agent to a mixture of the trans-vinylsulfide ketone (I), optically active oxazaborolidine (II) and the additive.

In the present invention, $R^1$ in the starting trans-vinylsulfide ketone (I) has the same meaning of X in the substituted thioazetidinone derivative (IV) disclosed in the above-mentioned JP-A-3-127773.

Namely, $R^1$ is a leaving group, together with the adjacent sulfur atom in the presence of a copper compound, and therefore, it is not specifically limited unless the substitution reaction with the carboxylic acid in the presence of the copper compound is inhibited. Nevertheless, in view of the easy availability and the cost, alkyl groups and aryl groups may be exemplified. The preferable examples of the alkyl groups are linear or branched lower alkyl group having a carbon number of 1 to 6, preferably 1 to 4, such as a methyl, ethyl, n-propyl, isopropyl, n-butyl, tert-butyl or hexyl group. The preferable examples of the aryl groups are those having 6 to 10 carbon atoms, for example, a phenyl group; phenyl groups substituted, at the 3- or 4-position, with one or more of halogen atoms such as fluorine or chlorine atom, nitro groups, lower alkyl groups such as methyl, ethyl, n-propyl, isopropyl, n-butyl, tert-butyl or hexyl groups or lower alkoxy groups such as methoxy or ethoxy groups; a tolyl group; a xylyl group; naphthyl group.

Note that the term "lower" means herein a carbon atom number of, preferably 1 to 8, more preferably 1 to 4, unless otherwise specified.

The optically active oxazaborolidines (II) to be used in the present invention are known catalysts, as disclosed in, for example, E. J. Corey et al., J. Am. Chem. Soc., 109, 7925–7926 (1987); E. J. Corey et al., J. Am. Chem. Soc., 109, 5551–5553 (1987); E. J. Corey et al., J. Org. Chem., 53, No. 12, 2861–2863 (1988); E. J. Corey et al., Tetrahedron Lett., 30, No. 46, 6275–6278 (1989); E. J. Corey et al., Tetrahedron Lett., 31, No. 5, 611–614 (1990); EP-A-305180; D. J. Mathre et al., J. Org. Chem., 56, No. 2, 751–762 (1991); S. Wallbaum et al., Tetrahedron:Asymmetry, 3, No. 12, 1475–1504 (1992); JP-A-4-224556.

In the present invention, the preferable examples of $R^2$ are a hydrogen atom; a linear or branched lower alkyl group having 1 to 4 carbon atoms such as methyl, ethyl, n-propyl, isopropyl, n-butyl or tert-butyl group; aryl groups having 6 to 10 carbon atoms such as a phenyl group, phenyl groups substituted, at the 3- or 4-position, with one or more of halogen atoms such as a fluorine or chlorine atom, lower alkyl groups such as methyl, ethyl, n-propyl, isopropyl, n-butyl, tert-butyl or hexyl groups, a trifluoromethyl group or lower alkoxy groups such as methoxy or ethoxy groups, a tolyl group, a xylyl group, a 2-naphthyl group and aralkyl groups having 7 to 14 carbon atoms such as benzyl or phenetyl groups. The especially preferable substituents are methyl and phenyl groups.

The preferable examples of $R^3$ and $R^4$ are linear, branched or cyclic alkyl groups having 1 to 8 carbon atoms, more preferably 3 to 8 carbon atoms, such as methyl, ethyl, n-propyl, isopropyl, n-butyl, tert-butyl, hexyl, 2,2-dimethyl-1-propyl, cyclohexyl, cyclopentylmethyl or 1,1,3,3-tetramethyl-1-butyl groups; aryl groups having 6 to 10 carbon atoms such as a phenyl group, phenyl groups substituted with, at the 3- or 4-position, one or more of halogen atoms such as a fluorine or chlorine atom, lower alkyl groups such as methyl, ethyl, n-propyl, isopropyl, n-butyl, tert-butyl or hexyl groups, a trifluoromethyl group, or lower alkoxy groups such as methoxy or ethoxy groups, a tolyl group, a xylyl group, a 2-naphthyl group; and aralkyl groups having 7 to 14 carbon atoms such as benzyl or phenethyl groups. The especially preferable groups are alkyl groups having 3 to 8 carbon atoms and a phenyl group. Furthermore, the compounds having the same group for $R^3$ and $R^4$ are preferable due to their easy synthesis. The phenyl group is especially preferable. Typical examples of the optically active oxazaborolidines (II) are (S)-3,3-diphenyl-1-methyltetrahydro-1H,3H-pyrrolo[1,2-c][1,3,2] oxazaborol, (S)-1,3,3-triphenyltetrahydro-1H,3H-pyrrolo[1,2-c][1,3,2] oxazaborol.

Furthermore, the optically active oxazaborolidines (II) can be easily produced from easily available proline by a known method (see D. J. Mathre et al., J. Org. Chem., 56, No. 2, 751–762 (1991); EP-A-0305180; JP-A-4-224556; JP-A-6-41012). For example,

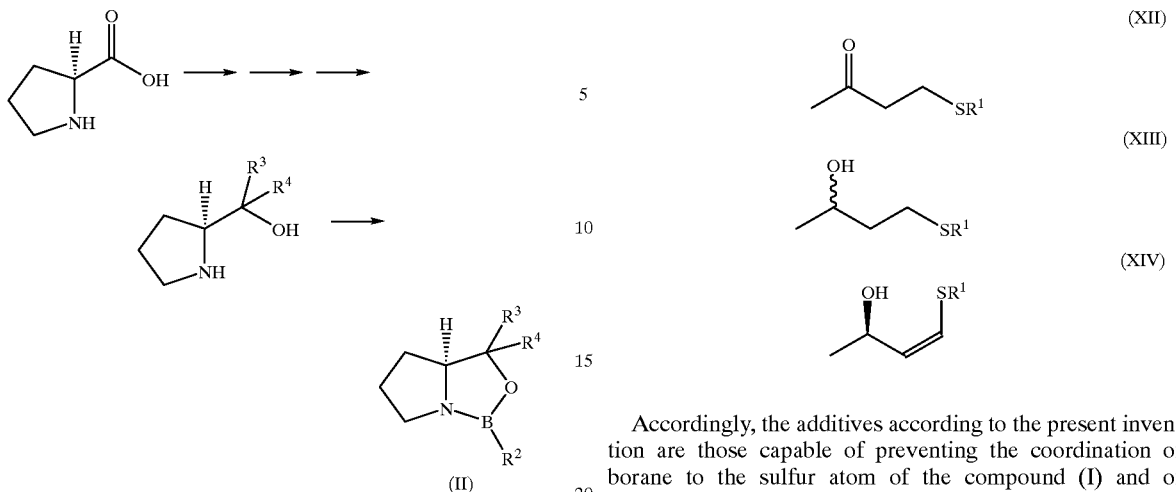

When optically active α,α-diphenyl-2-pyrrolidine methanol obtained from optically active proline by a known method is reacted with borane, the compound having a hydrogen atom for $R^2$, and phenyl groups for $R^3$ and $R^4$ can be obtained. Similarly, when reacted with trimethylboroxine, the compound having a methyl group for $R^2$ can be obtained and, when reacted with phenylboric acid, the compound having a phenyl group for $R^2$ can be obtained. Note that the commercially available optically active α,α-diphenyl-2-pyrrolidine methanol can also be used.

The optically active oxazaborolidine (II) is used in an amount of not more than stoichiometrical amount but sufficient amount to convert the reactants to the desired product. The amount is determined taking into consideration the prevention or suppression of the generation of the reduction with the noncatalytic reaction, i.e., the non-selective reduction. The preferable amount is 0.05 to 0.1 equivalent amount to the trans-vinylsulfide ketone (I).

As examples of the borane reducing agent to be used as the reducing agent, catechol borane (CB), borane dimethylsulfide complex (BMS), borane tetrahydrofuran complex (BTHF), can be exemplified. Among these, BMS is especially preferable. The amount of the reducing agent used is determined taking into consideration the prevention or suppression of the generation of the reduction with the noncatalytic reaction, i.e., the nonselective reduction, preferably 0.34 to 1.0 equivalent amount to the trans-vinylsulfide ketone (I).

The additives according to the present invention are defined as the reagent capable of controlling the reduction of the olefin double bond in the starting trans-vinylsulfide ketone (I) in the production method of the present invention. By the use of this additive, the reaction proceeds efficiently under the mild conditions. Namely, when the reaction is carried out by adding the borane reducing agent to a mixture of the trans-vinylsulfide ketone (I) and the optically active oxazaborolidine (II), the following two types of the compounds (XII) and (XIII) obtained by the reduction of the olefin double bond are by-produced. This is believed that the olefin double bond near the sulfur atom, which coordinate to borane reducing agent, of the compound (I) is directly attacked by the hydride ion. Furthermore, a large amount of the cis-isomer (XIV) of the desired trans-product is produced as a by-product.

Accordingly, the additives according to the present invention are those capable of preventing the coordination of borane to the sulfur atom of the compound (I) and of possessing a coordination power such that the reducing capability of borane is not inhibited. The preferable additives and the amounts to be used can be appropriately selected depending upon the compound (I), the oxazaborolidine (II) and the borane reducing agent. The preferable examples of the additives are sulfide compounds etc. The typical examples are dimethylsulfide, methylphenylsulfide, diphenylsulfide, di-n-butylsulfide, di-sec-butylsulfide, di-tert-butylsulfide, dibenzylsulfide. The preferable amount used is 0.5 to 5.0 equivalent amount to the trans-vinylsulfide ketone (I).

The reaction can be carried out in an appropriate inert solvent. The inert solvents mean those which can sufficiently dissolve the reactants, the desired product, the optically active oxazaborolidine and the additives and which are not provide an interaction to the intended reaction. Examples of the preferable solvents are aprotic non-basic solvent, for example, ethers such as tetrahydrofuran, tetrahydropyran, dimethyl ether, diethyl ether, 1,2-dimethoxyethane, dioxane; acyclic or cyclic saturated hydrocarbons such as n-hexane, cyclohexane; aromatic hydrocarbons such as benzene, toluene, xylene; halogenated hydrocarbons such as dichloromethane. The especially preferable examples are nonpolar solvents such as toluene, n-hexane, cyclohexane, xylene.

The reaction is carried out in a manner such that the catalytic reaction rate is controlled by adding the borane reducing agent in the above-mentioned nonpolar solvent to a mixture of the trans-vinylsulfide ketone (I), the optically active oxazaborolidine (II) and the additive in the above solvent at a temperature of −10° C. to a room temperature usually for 30 minutes to 2 hours. Then, the reaction is terminated by adding a reaction terminator such as aqueous saturated ammonium chloride solution.

Note that, during the reaction, it is desirable to prevent the suppression of the inactivation of the borane reducing agent and the deactivation of the catalyst and to decrease the water content in the reaction system to suppress the decrease in the optical yield as much as possible. Namely, in the preferable embodiment of the reaction according to the present invention, the reaction is carried out in a dehydrated condition, for example, in the presence of a desiccant. Examples of the preferable dehydrating agent are molecular sieve 4A (MS4A available from Nacalai Tesque Inc.), molecular sieve 3A (MS3A), molecular sieve 5A (MS5A), and inorganic compounds such as magnesium sulfate, sodium sulfate, potassium carbonate.

The reaction is carried out in an inert gas atmosphere such as nitrogen gas or argon gas.

After the completion of the reaction, the optically active trans-vinylsulfide alcohol (III) can be used, as the concentrated crude extract for the subsequent step by washing and drying the reaction mixture in a conventional manner, followed by evaporating off the solvent. If necessary, the product can be purified by recrystallization or chromatography such as liquid chromatography.

The optically active trans-vinylsulfide alcohol (III) obtained above are, after protecting the hydroxy group at the 3-position, converted to the substituted thioazetidinone derivative (XI) by the cyclization reaction with chlorosulfonyl isocyanate (CSI).

The protective group of the hydroxy group is not specifically limited and any conventionally used protective groups may be appropriately selected. Examples of the preferable protective group are tri-substituted silyl groups such as trialkylsilyl group, aryl (alkyl) alkoxysilyl group, alkoxydiarylsilyl group, triarylsilyl group, alkyldiarylsilyl group, aryldialkylsilyl group, triaralkylsilyl group. More specifically, trimethylsilyl group, triethylsilyl group, triisopropylsilyl group, dimethylhexylsilyl group, tert-butyldimethylsilyl group, methyldiisopropylsilyl group, isopropyldimethylsilyl group, tert-butylmethoxyphenylsilyl group, tert-butoxydiphenylsilyl group, triphenylsilyl group, tert-butyldiphenylsilyl group, dimethylcumylphenylsilyl group, tribenzylsilyl group can be exemplified. The especially preferable protective group is tert-buthyldimethylsilyl group. The protecting method is varied depending upon the nature or property of the protective group. For example, when the hydroxy group is protected with a tert-butyldimethylsilyl group, the protecting reaction can be carried out by reacting 1 to 2 equivalent amount, based upon the hydroxy group, of tert-butyldimethylchlorosilane in the presence of a catalyst such as a tertiary amine (e.g., triethylamine), 4-dimethylaminopyridine according to a known method (see Tetrahedron Lett., No. 2, 99–102 (1979)). In this reaction, amides such as N,N-dimethylformamide, ketones such as acetone, methylethyl ketone, ethers such as tetrahydrofuran, diethyl ether, aromatic hydrocarbons such as benzene, toluene, xylene, or any mixture thereof, may be preferably used as a solvent. After the completion of the reaction, the reaction mixture is diluted with an organic solvent immiscible with water and then washed with an aqueous saturated potassium hydrogen sulfate solution, water, an aqueous saturated sodium hydrogen carbonate solution, and saturated brine, in this order, followed by evaporating off the solvent. Thus, the trans-vinylsulfide (IX) having the protected hydroxy group at the 3-position.

The trans-vinylsulfide ketones (I) usable as the starting material in the present invention may be easily produced by various known methods, but the following two methods are exemplified as the excellent method for efficiently obtaining the trans compounds suitable for use in the reaction of the present invention at a low cost under mild conditions.

First method:

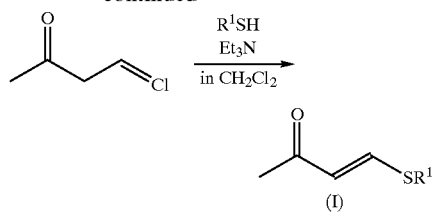

Namely, according to this method, acetyl chloride is reacted with acetylene in the presence of aluminum chloride to prepare the chlorovinyl ketone. The resultant chlorovinyl ketone is condensated with mercaptan to obtain the desired trans-vinylsulfide ketone (I).

Second method:

This method can refer to R. K. Haynes et al., Aust. J. Chem., 41, 881–895 (1988).

EXAMPLES

The present invention will now be further illustrated by, but is by no means limited to, the following Examples.

The NMR spectra of the compounds obtained in the following Preparation Examples and Examples were measured by ALPHA-500 (manufactured by JEOL, Japan). The solvent used was deuterio chloroform and tetramethylsilane was used as an internal standard. The melting point (mp) was determined by micro melting point apparatus (manufactured by Yanagimote Seisakusho, Japan).

As the column chromatography, silica gel (Kiesel gel 60 (Art. 7734) available from Merck Co.) was used.

The reaction solvent was dried by molecular sieve (i.e., pellet form (1/16) available from Nacalai Tesque Inc.), and the reducing agent was used by diluting the commercially available product (available from Aldrich Co.) with dry toluene, followed by quantitative determination.

The conditions of high performance liquid chromatography (HPLC) used were as follows.

Column: Chiralcel OD 4.6×250 mm (manufactured by Daicel Chemical Industries Ltd.)
Column temperature: Room temperature
Detection wavelength: 254 nm
Eluent: n-hexane:isopropyl alcohol=95:5, provided that n-hexane:ethanol=98:2 in Example 8 and n-hexane:isopropyl alcohol=99.75:0.25 in Example 9.
Column speed: 0.6 ml/min, provided that 0.5 ml/min was used in Example 8 and 0.4 ml/min was used in Example 9.
Termination time: 40 minutes, provided that 80 minutes were used in Example 8 and 120 minutes were used in Example 9.

Preparation Example 1

Preparation of (S)-3,3-diphenyl-1-methyltetrahydro-1H,3H-pyrrolo[1,2-c]1,3,2 oxazaborol Under argon stream, to a solution of (S)-α,α-diphenyl-2-pyrrolidine methanol (3 g, 11.8 mmol) in dry toluene (90 ml)

was added trimethyl boroxine (1.13 ml, 8.0 mmol), followed by stirring for 1.5 hours. After the argon stream was stopped and the toluene (22.5 ml) was recovered under normal pressures on an oil bath at 140° C., dry toluene (22.5 ml) was added. Furthermore, after this recovery operation was repeated twice, the resultant product was concentrated under normal pressures, and subsequently under a reduced pressure, to thereby obtain the titled compound as a colorless crystalline.

Yield: 3.28 g (yield 100%);

NMR($\delta$ ppm): 0.36 (3H, s, methyl at 1-position), 0.77–0.86 (1H, m, 1 proton of methylene at 4-position), 1.55–1.79 (3H, m, 1 proton of methylene at 4-position, methylene at 5-position), 3.02–3.07 (1H, m, 1 proton of methylene at 6-position), 3.32–3.37 (1H, m, 1 proton of methylene at 6-position), 4.35 (1H, dd, methine at 3a-position), 7.13–7.62 (10H, m, ArH)

Preparation Example 2

Preparation of (E)-4-phenylthio-3-buten-2-one

To a solution of (E)-4-methoxy-3-buten-2-one (purity 90%, 5.66 ml, 49.9 mmol) and thiophenol (5.13 ml, 49.9 mmol) in benzene (60 ml) was added p-toluene 25 sulfonic acid-monohydrate (30 mg, 0.16 mmol), followed by heating while stirring on an oil bath at 55° C. for 30 minutes. After ice cooling, an aqueous saturated sodium hydrogen carbonate solution was added thereto, followed by extracting with cyclohexane 3 times. The organic layer was washed with an aqueous saturated sodium hydrogen carbonate solution twice and with saturated brine, followed by drying with anhydrous magnesium sulfate. After concentrating under a reduced pressure, the residue was treated with the column chromatography (190 g, n-hexane:ethyl acetate=10:1). After evaporated under a reduced pressure, the titled compound was recrystallized from n-hexane-n-nonane to obtain as a colorless crystalline.

Yield: 3.04 g (yield 34.1%);

mp: 37.5–38.5° C.;

NMR($\delta$ ppm): 2.20 (3H, s, methyl at 1-position), 6.02 (1H, d, olefin at 3-position), 7.39–7.49 (5H, m, ArH), 7.70 (1H, d, olefin at 4-position)

Preparation Example 3

Preparation of (E)-4-(2-naphthylthio)-3-buten-2-one

To a solution of (E)-4-methoxy-3-buten-2-one (purity: 90%, 15.0 ml, 0.13 mol) and 2-naphthalenethiol (21.16 g, 0.13 mol) in benzene (180 ml) was added p-toluene sulfonic acid-monohydrate (75 mg, 0.4 mmol), followed by heating, while stirring, on an oil bath at 50° C. for 70 minutes. After ice cooling, an aqueous saturated sodium hydrogen carbonate solution was added thereto, followed by extracting with ethyl acetate four times. The ethyl acetate layer was washed with an aqueous saturated sodium hydrogen carbonate solution and saturated brine twice and then dried with anhydrous magnesium sulfate. After concentrating under a reduced pressure, the residue was treated with the column chromatography (670 g, n-hexane:methylene chloride:ethyl acetate=1:0:0–1:3:0–2:0:1), followed by recrystallizing from n-hexane-ethyl ether to thereby obtain the titled compound as a light brown crystalline.

Yield: 5.04 g (yield 16.7%);

mp: 62–64° C.;

NMR($\delta$ ppm): 2.19 (3H, s, methyl at 1-position), 6.03 (1H, d, olefin at 3-position), 7.78 (1H, d, olefin at 4-position), 7.50–7.57, 7.82–8.00 (7H, m, ArH)

Preparation Example 4

Preparation of (E)-4-(tert-butylthio)-3-buten-2-one

To a solution of (E)-4-methoxy-3-buten-2-one (purity: 90%, 7.92 ml, 69.9 mmol) and tert-butylmercaptan (5.54 ml, 48.9 mmol) in carbon tetrachloride (70 ml) was added, under ice cooling, trifluoroacetic acid (7.54 ml, 97.9 mmol), followed by heating, under reflux, on an oil bath at 95° C. for 4 hours. After ice cooling, ethyl ether was added 5 thereto, followed by washing with water (twice), an aqueous saturated sodium hydrogen carbonate solution, water and saturated brine. After drying with anhydrous magnesium sulfate, the resultant product was concentrated under a reduced pressure and the residue was treated with the column chromatography (420 g, n-hexane:ethyl acetate=1:0–6:1) to thereby obtain the titled compound in the form of a pale yellow oil.

Yield: 6.93 g (yield 89.6%);

NMR($\delta$ ppm): 1.44 (9H, s, $(CH_3)_3C$), 2.21 (3H, s, methyl at 1-position), 6.31 (1H, d, olefin at 3-position), 7.81 (1H, d, olefin at 4-position)

Example 1

Preparation of (R,E)-4-phenylthio-3-buten-2-ol (E)-4-phenylthio-3-buten-2-one (178 mg, 1.0 mmol), (S)-3,3-diphenyl-1-methyltetrahydro-1H,3H-pyrrolo[1,2-c][1,3,2] oxazaborol (28 mg, 0.1 mmol) and MS4A (Nacalai Tesque Inc., 500 mg) were dried by a vacuum pump, followed by substituting with an argon gas. Dry toluene (5 ml) and dimethylsulfide (3.0 mmol) were added thereto and, after ice cooling, a solution of borane dimethylsulfide complex in toluene (1.07M, 0.65 ml, 0.7 mmol) was dropwise added. After stirring for two hours, an aqueous saturated ammonium chloride solution was added, followed by filtering through a cotton plug. The filtrate was washed with ethyl acetate and, after separating an aqueous layer, the organic layer was washed with 2NHCl, water, an aqueous saturated sodium hydrogen carbonate solution, water and saturated brine. After drying with anhydrous magnesium sulfate, the extract containing the titled compound as a main component was obtained by concentrating under a reduced pressure. The NMR chemical shifts of the titled compound are as follows.

NMR($\delta$ ppm): 1.31 (3H, d, methyl at 1-position), 1.51 (1H, brs, OH), 4.40 (1H, m, methine at 2-position), 5.89 (1H, dd, olefin at 3-position), 6.42 (1H, d, olefin at 4-position), 7.23–7.38 (5H, m, ArH)

Further, the extract obtained by the concentration under a reduced pressure was analyzed by HPLC to obtain the yields of the desired compound and the by-products. The results are shown in Table I. Furthermore, as Comparative Example, the extract obtained by the similar method as mentioned above, except that the dimethylsulfide as the additive was not used, was analyzed in the same manner. The results are shown in Table I.

TABLE I

| | Yield (%) | | | |
|---|---|---|---|---|
| Compound No. | (III) (ee) | (XII) | (XIII) | (XIV) |
| Example 1 | 70 (90) | 9 | 10 | 4 |
| Comparative Example | 59 (89) | 16 | 13 | 12 |

Examples 2–4

Preparation of (R,E)-4-phenylthio-3-buten-2-ol

The results shown in Table II were obtained in the same manner as in Example 1, except that, instead of the dimethylsulfide as the additive, methylphenylsulfide (Example 2), diphenylsulfide (Example 3) and di-tert-butylsulfide (Example 4) were used, respectively.

TABLE II

| Compound No. | Yield (%) | |
|---|---|---|
| | (III) (ee) | (XIV) |
| Example 2 | 67 (88) | 2 |
| Example 3 | 65 (89) | 2 |
| Example 4 | 61 (89) | 8 |

Examples 5–7

Preparation of (R,E)-4-phenylthio-3-buten-2-ol

The results shown in Table III were obtained in the same manner as in Example 1, except that cyclohexane (Example 5), n-hexane (Example 6) and xylene (Example 7) were used, respectively, as a solvent, instead of the toluene.

TABLE III

| Compound No. | Yield (%) (III) (ee) |
|---|---|
| Example 5 | 71 (89) |
| Example 6 | 73 (87) |
| Example 7 | 65 (89) |

Example 8

Preparation of (R,E)-4-(2-naphtylthio)-3-buten-2-ol (E)-4-(2-naphthylthio)-3-buten-2-one (228 mg, 1.0 mmol), (S)-3,3-diphenyl-1-methyltetrahydro-1H,3H-pyrrolo[1,2-c][1,3,2] oxazaborol (28 mg, 0.1 mmol) and MS4A (500 mg) were dried by a vacuum pump, followed by substituting with an argon gas. Dry toluene (5 ml) and dimethylsulfide (0.22 ml, 3.0 mmol) were added thereto and, after ice cooling, a solution of borane dimethylsulfide complex in toluene (1.07M, 0.65 ml, 0.7 mmol) was dropwise added. After stirring for two hours, an aqueous saturated ammonium chloride solution was added, followed by filtering through a cotton plug.

The filtrate was washed with ethyl acetate and, after separating an aqueous layer, the ethyl acetate layer was washed with 2NHCl, water, an aqueous saturated sodium hydrogen carbonate solution, water and saturated brine. After drying with anhydrous magnesium sulfate, the extract containing the titled compound as a main component was obtained by concentrating under a reduced pressure. The NMR chemical shifts of the titled compound are as follows. Further, the HPLC analytical results are shown in Table IV.

NMR(δ ppm): 1.33 (3H, d, methyl at 1-position), 1.53 (1H, d, OH), 4.44 (1H, m, methine at 2-position), 5.94 (1H, dd, olefin at 3-position), 6.52 (1H, d, olefin at 4-position), 7.43–7.51, 7.77–7.82 (7H, m, ArH)

TABLE IV

| Compound No. | Yield (%) | |
|---|---|---|
| | (III) (ee) | (XIV) |
| Example 8 | 72 (93) | 2 |

Example 9

Preparation of (R,E)-4-(tert-butylthio)-3-buten-2-ol (S)-3,3-diphenyl-1-methyltetrahydro-1H,3H-pyrrolo[1,2-c][1,3,2] oxazaborol (28 mg, 0.1 mmol) and MS4A (Nacalai Tesque Inc., 500 mg) were dried by a vacuum pump, followed by substituting with an argon gas. To this mixture, (E)-4-(tert-butylthio)-3-buten-2-one (158 mg, 1.0 mmol) and dimethylsulfide (0.22 ml, 3.0 mmol) were added, which were then washed into the mixture with dry toluene (5 ml). After ice cooling, a solution of borane dimethylsulfide complex in toluene (1.07M, 0.65 ml, 0.7 mmol) was dropwise added. After stirring for two hours, an aqueous saturated ammonium chloride solution was added, followed by filtering through a cotton plug. The filtrate was washed with ethyl acetate and, after separating an aqueous layer, the ethyl acetate layer was washed with 2NHCl, water, an aqueous saturated sodium hydrogen carbonate solution, water and saturated brine. After drying with anhydrous magnesium sulfate, the extract containing the titled compound as a main component was obtained by concentrating under a reduced pressure. The NMR chemical shifts of the titled compound are as follows. Further, the HPLC analytical results are shown in Table V.

NMR(δ ppm): 1.29 (3H, d, methyl at 1-position), 1.35 (9H, s, (CH$_3$)$_3$C), 1.46 (1H, d, OH), 4.36 (1H, m, methine at 2-position), 5.87 (1H, dd, olefin at 3-position), 6.36 (1H, d, olefin at 4-position)

TABLE V

| Compound No. | Yield (%) | |
|---|---|---|
| | (III) (ee) | (XIV) |
| Example 9 | 64 (88) | 8 |

INDUSTRIAL APPLICABILITY

According to the present invention, since the production of the optically active trans-vinylsulfide alcohol useful as the synthetic material of penem or carbapenem compounds, can be efficiently carried out under a mild condition with a simplified steps and the improvement in the yield can be realized due to the fact that the present invention is not an optical resolution method of a racemic mixture, and therefore, the present invention is industrially advantageous. Furthermore, the compounds obtained at a high yield and a high selectivity according to the present invention have a trans-isomer structure and provide excellent yield and selectivity in the subsequent step and, as a result, the improvement can be obtained in the synthesis of penem or carbapenem compounds.

We claim:

1. A method for producing an optically active trans-vinylsulfide alcohol having the formula (III):

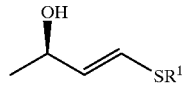

wherein R$^1$ represents an alkyl group or an aryl group, comprising the step of reducing a trans-vinylsulfide ketone having the formula (I):

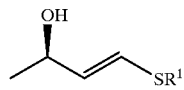

wherein $R^1$ is the same as defined above with a borane reducing agent in the presence of an optically active oxazaborolidine having the formula (II):

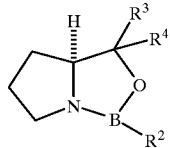

wherein $R^2$ represents a hydrogen atom, an alkyl group, an aryl group or an aralkyl group and $R^3$ and $R^4$ are the same or different and represent an alkyl group, an aryl group or an aralkyl group in the presence of at least one sulfide compound selected from the group consisting of dimethylsulfide, methylphenylsulfide, diphenylsulfide, di-n-butylsulfide, di-sec-butylsulfide, di-tert-butylsulfide and dibenzylsulfide as an additive for controlling the reduction of the olefin double bond of the trans-vinylsulfide ketone, wherein said additive prevents coordination of the borane reducing agent to the sulfur atom of the trans-vinylsulfide ketone (I).

2. A method as claimed in claim 1, wherein $R^1$ is a phenyl group or a phenyl group substituted with one or more of halogen atoms, nitro groups, lower alkyl groups or lower alkoxy groups.

3. A method as claimed in claim 1, wherein $R^1$ is a phenyl group.

4. A production method as claimed in claim 1, wherein $R^2$ is a hydrogen atom, a lower alkyl group, a phenyl group, or a phenyl group substituted with one or more of halogen atoms, lower alkyl groups, trifluoromethyl groups or lower alkoxy groups.

5. A method as claimed in claim 1, wherein $R^2$ is a methyl group or a phenyl group.

6. A method as claimed in claim 1, wherein $R^3$ and $R^4$ are the same alkyl groups, aryl groups or aralkyl groups.

7. A method as claimed in claim 1, wherein $R^3$ and $R^4$ are 2-naphthyl groups, phenyl groups, phenyl groups substituted with one or more of halogen atoms, lower alkyl groups, trifluoromethyl groups or lower alkoxy groups.

8. A method as claimed in claim 1, wherein $R^3$ and $R^4$ are phenyl groups.

9. A method as claimed in claim 1, wherein the borane reducing agent is a borane dimethylsulfide complex.

10. A method as claimed in claim 2, wherein $R^2$ is a hydrogen atom, a lower alkyl group, a phenyl group, or a phenyl group substituted with one or more of halogen atoms, lower alkyl groups, trifluoromethyl groups or lower alkoxy groups.

11. A method as claimed in claim 3, wherein $R^3$ is a methyl group or a phenyl group.

12. A method as claimed in claim 10, wherein $R^3$ and $R^4$ are the same alkyl groups, aryl groups or aralkyl groups.

13. A method as claimed in claim 12, wherein $R^3$ and $R^4$ are 2-naphthyl groups, phenyl groups, phenyl groups substituted with one or more of halogen atoms, lower alkyl groups, trifluoromethyl groups or lower alkoxy groups.

14. A method as claimed in claim 14, wherein $R^3$ and $R^4$ are phenyl groups.

15. A method as claimed in claim 12, wherein $R^3$ and $R^4$ are phenyl groups.

16. A method as claimed in claim 13, wherein the borane reducing agent is a borane dimethylsulfide complex.

17. A method as claimed in claim 15, wherein the borane reducing agent is a borane dimethylsulfide complex.

* * * * *

UNITED STATES PATENT AND TRADEMARK OFFICE
CERTIFICATE OF CORRECTION

PATENT NO. : 6,049,009
DATED : April 11, 2000
INVENTOR(S) : Kazuto Sekiuchi et al.

It is certified that error appears in the above-identified patent and that said Letters Patent is hereby corrected as shown below:

Claim 1,
Lines 19-22, please delete "as an additive for controlling the reduction of the olefin double bond of the trans-vinylsulfide ketone, wherein said additive prevents coordination of the borane reducing agent to the sulfur atom of the trans-vinylsulfuide ketone(I)."

Signed and Sealed this

Eighteenth Day of September, 2001

Attest:

*Nicholas P. Godici*

NICHOLAS P. GODICI
*Acting Director of the United States Patent and Trademark Office*

*Attesting Officer*